United States Patent [19]
Szyf et al.

[11] Patent Number: 5,919,772
[45] Date of Patent: Jul. 6, 1999

[54] ANTISENSE OLIGONUCLEOTIDES HAVING TUMORIGENICITY-INHIBITING ACTIVITY

[75] Inventors: Moshe Szyf, Cote St. Luc, Canada; Eric von Hofe, Wellesley, Mass.

[73] Assignees: McGill University, Montreal, Canada; Hybridon, Inc., Milford, Mass.

[21] Appl. No.: 08/481,876

[22] Filed: Jun. 7, 1995

Related U.S. Application Data

[62] Division of application No. 08/161,673, Dec. 1, 1993, Pat. No. 5,578,716.

[51] Int. Cl.$^6$ .............................. A61K 48/00; C07H 21/04
[52] U.S. Cl. .............................................. 514/44; 536/24.5
[58] Field of Search ................................ 514/44; 536/24.5

[56] References Cited

FOREIGN PATENT DOCUMENTS

WO 92/06985  4/1992  WIPO .
WO 92/15680  9/1992  WIPO .

OTHER PUBLICATIONS

MacLeod (1993) *Molecular Biology of the Cell 4* (Suppl.) 193A:1126.
Rouleau et al. *J. Biol. Chem.* (1992) 267:7368–7377.
Li et al. (1992) *Cell* 69:915–926.
Razin et al. (1984) *Biochim. Biophys. Acta* 782:331–342.
Szyf et al. (1992) *J. Biol. Chem.* 267:12831–12836.
Szyf et al. (1985) *J. Biol. Chem.* 260:8653–8656.
Szyf et al. (1991) *J. Biol. Chem.* 266:10027–10030.
Ohtani–Fukita et al. (1993) *Oncogone* 8:1063–1967.
Feinberg et al. (1988) *Cancer Res.* 48:1159–1161.
Goelz and Vogelstein (1985) *Science* 228:187–190.
Feinberg and Vogelstein (1983) *Nature* 301:89–92.
Agrawal (1992) *Trends in Biotech* 10:152.
Stephenson and Zamenick (1978) *Proc. Natl. Acad. Sci. USA* 75:285.
Leonetti et al. (1988) *Gene* 72:323.
Burch and Mahan (1991) *J. Clin. Invest.* 88:1190.
Jones and Buckley (1990) *Adv. In Cancer Res.* 54:1–23.
Yen et al. (1992) *Nucl. Acids. Res.* 9:2287–2291.
Szyf et al. (1989) *Proc. Natl. Acad. Sci. USA* 86:6853–6857.
Szyf et al. (1990) *Mol. Endocrin* 4:1144–1152.
Zakut–Houri et al. (1983) *Nature* 306:594–597.
Gura, Science, 270:575–577 (1995).
Rojanasakul, Advanced Drug Delivery Reviews, 18:115–131 (1996).
Bennett, Science, 271:434 (1996).
Miller et al., Parasitology Today, 10(3):92–97 (1994).
Wu–Pong, Pharmaceutical Technology, 18:102–114 (1994).
Stull et al., Pharmaceutical Research, 12(4):465–483 (1995).
Wagner, Nature, 372:333–335 (1994).
Weiss, Science News, 139:108–109 (1991).
Westerman et al., Biomed. Biochem. Acta., 48(1):85–93 (1989).
Stein, CA et al., Science, 261:1004–1012 (1993).
Milligan, JF et al., Journal of Medicinal Chemistry, 36(14):1923–1937 (1993).
Uhlmann, E et al., Chemical Reviews, 90(4):543–584 (1990).
Szyf, M et al., Journal of Biological Chemistry, 267(18):12831–12836 (1992).
Macleod, AR et al., Journal of Biological Chemistry, 270(14):8037–8043 (1995).
El–Diery, WS et al., Proc. Natl. Acad. Sci USA, 88:3470–3474 (1991).
Baylin, SB et al., Cancer Cells, 3(10):383–390 (1991).

*Primary Examiner*—Bruce R. Campell
*Attorney, Agent, or Firm*—Hale and Dorr LLP

[57] ABSTRACT

The invention encompasses tumorigenicity-inhibitiig antisense oligonucleotide sequences complementary to mRNA or double-stranded DNA that encodes mammalian DNA methyl transferase. It further encompasses methods for inhibiting tumorigenicity and pharmaceutical composition comprising the tumorigenicity-inhibiting antisense nucleotide.

8 Claims, 4 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iv) ANTI-SENSE: YES (xi) SEQUENCE DESCRIPTION: SEQ ID NO:1:

CATCTGCCAT TCCCACTCTA                                          20

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (iv) ANTI-SENSE: YES (xi) SEQUENCE DESCRIPTION: SEQ ID NO:2:

TTGGCATCTG CCATTCCCAC TCTA                                     24

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..19
      (D) OTHER INFORMATION: /note= "5' PRIMER BASES 154-172"

(xi) SEQUENCE DESCRIPTION: SEQ ID NO:3:

TCCGAATCGG TTTCCACCC                                           19

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..21
      (D) OTHER INFORMATION: /note= "3' PRIMER BASES 472-492"

(xi) SEQUENCE DESCRIPTION: SEQ ID NO:4:

GGAGGATGAG GGCCTGAATG C                                        21

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..18
        (D) OTHER INFORMATION: /note= "PRIMER 1-18"

(xi) SEQUENCE DESCRIPTION: SEQ ID NO:5:

```
GGACTGGGGT GAGGACGG                                                18
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /note= "PRIMER 620-610"

(xi) SEQUENCE DESCRIPTION: SEQ ID NO:6:

```
TTTCAGTAGA TAACGCACTG CTGG                                         24
```

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..19
        (D) OTHER INFORMATION: /note= "ANTI SENSE PRIMER"

(xi) SEQUENCE DESCRIPTION: SEQ ID NO:7:

```
GCAAACAGAA TAAAGAATC                                               19
```

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..19
        (D) OTHER INFORMATION: /note= "SENSE PRIMER"

(xi) SEQUENCE DESCRIPTION: SEQ ID NO:8:

```
GTATGGTGGT TTGCCTGGT                                               19
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iv) ANTI-SENSE: YES (ix) FEATURE:
        (A) NAME/KEY: misc_feature
        (B) LOCATION: 1..20
        (D) OTHER INFORMATION: /note= "Oligo 34: DW2-34B
            (antisense phosphodiester)"

(xi) SEQUENCE DESCRIPTION: SEQ ID NO:9:

CATCTGCCAT TCCCACTCTA    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iv) ANTI-SENSE: YES (ix) FEATURE:
        (A) NAME/KEY: misc_feature
        (B) LOCATION: 1..20
        (D) OTHER INFORMATION: /note= "Oligo 35: DW2-35C
            (antisense phosphorothioate)"

(xi) SEQUENCE DESCRIPTION: SEQ ID NO:10:

CATCTGCCAT TCCCACTCTA    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /note= "Oligo 36: DW2-36C (Random
            Control Phosphodiester)"

(xi) SEQUENCE DESCRIPTION: SEQ ID NO:11:

CTGACTGCCA ACTATGAACA    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:

```
    (A) NAME/KEY: misc_feature
    (B) LOCATION: 1..20
    (D) OTHER INFORMATION: /note= "Oligo 37: DW2-37D (Random
          Control Phosphorothioate)"

(xi) SEQUENCE DESCRIPTION: SEQ ID NO:12:

CTGACTGCCA ACTATGAACA                                                        20
```

ANTISENSE OLIGONUCLEOTIDES HAVING TUMORIGENICITY-INHIBITING ACTIVITY

This is a divisional of application Ser. No. 08/161,673, filed Dec. 1, 1993, U.S. Pat. No. 5,578,716.

FIELD OF THE INVENTION

This invention relates to oligonucleotides for use in the inhibition of DNA methyl transferase expression, and more particularly, antisense inhibition of tumorigenicity.

DESCRIPTION OF RELATED ART

Alterations in the normal gene expression profile of a cell are thought to be early events in oncogenic transformation. A large number of oncogenes are transcription factors. However, many oncogenes are not transcription factors but are involved in signal transduction pathways that trigger activation of transcription factors such as the activation of Jun by the RAS signalling pathway.

The DNA methyltransferase (DNA MeTase) gene 5' region has recently been characterized (Rouleau et al, J. Biol. Chem., 267: 7368–7377 (1992)). It contains at least two functional AP-1 sites and the promoter of that gene can be dramatically transactivated by Fos, Jun or Ras. The DNA MeTase gene encodes an activity that is responsible for methylating cytosine residues in the dinucleotide sequence CpG. A hallmark of DNA methylation is that 80% of the CpG sites are methylated in a nonrandom manner generating a site-, tissue- and gene-specific pattern of methylation. Methylation patterns are formed during development. Establishment and maintenance (Razin and Szyf, Biochim. Biophys. Acta, 782: 331–342 (1984)) of the appropriate pattern of methylation is critical for development (Li et al., Cell, 69: 915–926 (1992)) and for defining the differentiated state of a cell (Szyf, et al., J. Biol. Chem., 267: 12831–12836 (1992)). The pattern of methylation is maintained by DNA MeTase at the time of replication (Szyf et al., J. Biol Chem., 260: 8653–8656 (1985)); the level of DNA MeTase activity and gene expression is regulated with the growth state of different primary and immortal cell lines (Szyf et al., J. Biol. Chem., 266: 10027–10030 (1991)).

The relationship of DNA methylation to tumorigenicity has been in a state of confusion for some time. Some reports have suggested that hypomethylation of certain genes may be implicated in neoplasia (see e.g., Ohtani-Fukita et al., Oncogene, 8: 1063–1967 (1993)). However many reports have demonstrated hypomethylation of total genomic DNA (see e.g., Feinberg et al., Cancer Res., 48: 1159–1161 (1988); Goelz and Vogelstein, Science, 228: 187–190 (1985)). Still other reports have connected hypomethylation of individual genes with tumorigenicity (see e.g., Feinberg and Vogelstein, Nature, 301: 89–92 (1983); Jones and Buckley, Adv. Can. Res., 54: 1–12 (1990)). Moreover, it has been suggested that current hypotheses about DNA methylation and cancer suggest that agents that reduce DNA methylation should cause transformation of cells (Jones and Buckley, supra). Thus, the prior art is devoid of any meaningful suggestion of how regulation of DNA methylation may be successfully manipulated to diminish tumorigenicity.

Antisense oligonucleotide technology has allowed for inhibition of expression of a variety of genes. See generally Agrawal, Trends in Biotech., 10: 152 (1992). By binding to the complementary nucleic acid sequence In RNA, antisense oligonucleotides are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17-mer base sequence statistically occurs only once in the human genome, and thus extremely precise targeting of specific sequences is possible with such antisense oligonucleotides.

In 1978 Zamecnik and Stephenson were the first to propose the use of synthetic antisense oligonucleotides for therapeutic purposes. Stephenson and Zamecnik, Proc. Natl. Acad. Sci. U.S.A., 75: 285 (1978); Zamecnik and Stephenson, Proc. Natl. Acad. Sci. U.S.A., 75: 280 (1978). They reported that the use of a oligonucleotide 13-mer complementary to the RNA of Rous sarcoma virus inhibited the growth of the virus in cell culture. Since then, numerous other studies have been published manifesting the in vitro efficacy of antisense oligonucleotide inhibition of viral growth, e.g., vesicular stomatitis viruses (Leonetti et al., Gene, 72: 323 (1988)), herpes simplex viruses (Smith et al, Proc. Natl. Acad. Sci. U.S.A., 83: 2787 (1986)), and influenza virus (Zerial et al., Nucleic Acids Res., 15: 9909 (1987)).

Antisense oligonucleotides have also been shown to inhibit protein expression from endogenous mammalian genes. For example, Burch and Mahan, J. Clin. Invest., 88: 1190 (1991), disclosed antisense oligonucleotides targeted to murine and human IL-1 receptors that inhibited IL-1-stimulated $PGE_2$ synthesis in murine and human fibroblasts, respectively; Colige et al., Biochemistry, 32: 7 (1993) disclosed antisense oligonucleotides that specifically inhibited expression of a mutated human procollagen gene in transfected mouse 3T3 cells without inhibiting expression of an endogenous gene for the same protein; and Monia et al., J. Biol. Chem., 267: 19954 (1992), disclosed selective inhibition of mutant Ha-ras mRNA expression with phosphorothioate antisense oligonucleotide.

Although antisense approaches have shown promise for a variety of disease states, there is no clear message about how or whether any genetic target exist that would allow successful use of antisense approaches to affect tumorigenicity. There is, therefore, a need to develop this promising technology in a way that might allow it to be applied in the fight against neoplasia.

SUMMARY OF THE INVENTION

Previous teachings have suggested that agents that inhibit DNA methylation should be capable of transforming cells (see e.g., Jones & Buckley, Adv. in Cancer Res., 54: 1–23 (1990)).

The present invention provides antisense oligonucleotides that surprisingly demonstrate tumorigenicity-inhibiting activity. The inventive oligonucleotides inhibit tumorigenisis by inhibiting expression of the gene encoding DNA methyl transferase. These oligonucleotides are complementary to mRNA or double-stranded DNA that encodes mammalian DNA methyl transferase. The present invention further provides useful compounds, compositions and methods for preventing the expression of the DNA methyl transferase gene. A still further object of the present invention is to provide compounds, compositions and methods for the treatment of and inhibition of tumorigenicity.

Accordingly, this disclosure presents antisense oligonucleotides that have been constructed and are targeted to bind to nucleic acid sequences encoding DNA MeTase, thereby blocking production of the expression product. Also presented are methods for inhibiting DNA MeTase expression and tumorigenesis.

The invention is useful in curing experimental mice of tumors. More specifically, the invention is useful in curing nude mice of human tumors, and, in particular, human small lung cell carcinoma. The invention may thus be used to avoid sacrificing an animal at the end of an experiment.

The present invention provides methods for inhibiting tumorigenesis by expressing an antisense message to the DNA MeTase in a cell line, and specifically in mouse and human cancer cell lines. Expression of an antisense DNA MeTase leads to: (i) a general reduction in the methylation content of the genome; (ii) demethylation of regions aberrantly methylated in a cell line such as the adrenal specific 21-hydroxylase gene as well as tumor suppressor loci; (iii) morphological changes indicative of inhibition of the transformed phenotype; (iv) inhibition of tumorigenesis in vitro as well as a loss of angiogenic function; and (vi) to the ability to undergo an apoptotic death program under appropriate conditions.

DETAILED DESCRIPTION OF THE PREFERRED EMBODIMENTS

Figure 1:
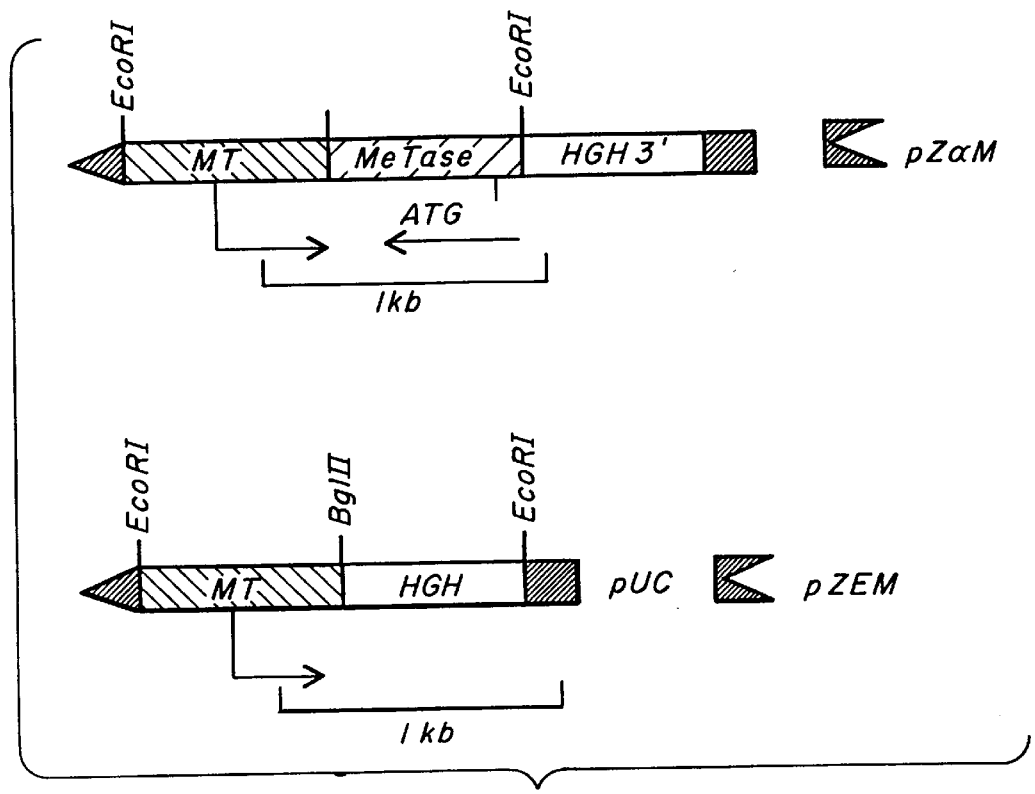
FIG. 1 is a physical map of the plasmids pZEM and pZαM. The metallothionine (MT) promoter (shaded box), the human growth hormone 3' region (HGH) (open bar), and the MeTase cDNA sequences (hatched) are indicated.

The invention provides antisense oligonucleotides that surprisingly inhibit tumorigenicity. These oligonucleotides are complementary to mRNA or double-stranded DNA that express mammalian, and, in particular, human or mouse, DNA methyl transferase and unexpectedly display tumorigenicity-inhibiting activity. Ones preferred antisense oligonucleotide of the present invention is 5'-CATCTGCCATTCCCACTCTA-3' (SEQ ID NO 1), having either phosphodiester or phosphorothioate linkages. Other suitable antisense oligonucleotides include the phosphorothioate: 5'-TTGGCATCTGCCATTCCCACTCTA-3' (SEQ ID NO 2).

Modified oligonucleotides having in vivo activity against tumorigenicity are referred to herein as anti-tumorigenicity or tumorigenicity-inhibiting modified oligonucleotides. The invention provides tumorigenicity-inhibiting modified oligonucleotides that have efficacy in inhibiting expression of DNA methyl transferase. Modified oligonucleotides according to the invention have specific preferred characteristics that are discussed in greater detail for each preferred embodiment below. In addition to these characteristics, modified oligonucleotides according to the invention may optionally have additional ribonucleotide, 2'-substituted ribonucleotide, and/or deoxyribonucleotide monomers, any of which are connected together via 5' to 3' linkages which may include any of the internucleotide linkages known in the art. Preferably, such modified oligonucleotides may optionally contain phosphodiester, phosphotriester, phosphoramidate, siloxane, carbonate, carboxymethylester, acetamidate, carbamate, thioether, bridged phosphoramidate, bridged methylene phosphonate, bridged phosphoramidate, bridged methylene phosphonate, bridged phosphorothioate and/or sulfone internucleotide linkages. Those skilled in the art will recognize that the synthesis of oligonucleotides containing any of these internucleotide linkages is well known to those skilled in the art, as is illustrated by articles by Uhlmann and-Peyman, *Chemical Reviews*, 90: 543–584 (1990) and Schneider and Banner, *Tetrahedron Lett.*, 21: 335 (1990) Preferably, modified oligonucleotides according to the invention should contain from about 6 to about 100 monomers in total and most preferably from about 12 to about 50 total monomers. Such modified oligonucleotides may also optionally contain modified nucleic acid bases and/or sugars, as well as added substituents, such as diamines, cholesteryl or other lipophilic groups.

Various preferred embodiments of modified oligonucleotides according to the invention are discussed below. Although these embodiments all have a nucleotide sequence from the same region of the DNA MeTase gene, those skilled in the art will recognize that the tumorigenicity-inhibiting efficacy of oligonucleotides having nucleotide sequences complementary to other essential nucleic acid sequences of DNA MeTase can also be enhanced by incorporating into such oligonucleotides the structural features of preferred embodiments of modified oligonucleotides according to the invention.

For purposes of the invention, complementary means having a sequence that hybridizes to the essential nucleic acid sequence under physiological conditions. An essential nucleic acid sequence of the DNA MeTase gene moans a nucleic acid sequence that is required for expressing DNA MeTase. For example, such oligonucleotides can have other sequences from the DNA MeTase gene. Indeed, any sequence from the DNA MeTase gone (the 5'-region as disclosed by Rouleau et al, *J. Biol. Chem.*, 267: 7368–7377 (1992) or Yen et al., *Nucl. Acids Res.*, 9: 2287–2291 (1992) should serve as the basis for modified oligonucleotides according to the invention. As a practical matter, the structural features of preferred embodiments of modified oligonucleotides according to the invention should enhance the tumorigenicity-inhibiting activity of any antisense oligonucleotide having a nucleotide sequence that hybridizes in a cell with any essential nucleic acid sequence of the DNA MeTase gene.

Each preferred embodiment of modified oligonucleotides according to the invention is separately discussed in greater detail below.

In a first preferred embodiment, tumorigenicity-inhibiting modified oligonucleotides according to the invention are in the form of a mixed backbone or chimeric oligonucleotide having one or more regions of nucleotides connected by phosphorothioate or phosphorodithioate internucleotide linkages ("phosphorothioate or phosphorodithioate region") as well as one or more regions of nucleotides connected by alkylphosphonate internucleotide linkages ("alkylphosphonate region"). In this embodiment, at least one alkylphosphonate region preferably includes nucleotides at or near the 5' end and/or the 3' end of the oligonucleotide. For purposes of the invention, "at or near" the 5' or the 3' end of the oligonucleotide means involving at least one nucleotide within about 5 nucleotides from the 5' or 3' end of the oligonucleotide. Preferably, the alkylphosphonate region comprises from about 2 to about 10 contiguous nucleotides connected by alkylphosphonate linkages. Preferably, the phosphorothioate or phosphorodithioate region comprises at least 3, and up to about 100 contiguous nucleotides connected by phosphorothioate or phosphorodithioate linkages. Many embodiments of oligonucleotides having this type of backbone structure are taught in U.S. Pat. Nos. 5,149,797 and 5,220,007, the teachings of which are hereby incorporated by reference.

Modified oligonucleotides having tumorigenicity-inhibiting activity according to this embodiment of the invention are synthesized by solid phase methods, alternating H-phosphonate chemistry and sulfur oxidation for phosphorothioate regions, and alkylphosphonamidate chemistry for alkylphosphonate regions. A preferred H-phosphonate approach is taught by Agrawal et al., U.S. Pat. No. 5,149,798, the teachings of which are hereby incorporated by reference. Alkylphosphonamidite chemistry is well known in the art, as illustrated by Agrawal and Goodchild, *Tetrahedron Lett.*, 28: 3539–3542 (1987). synthesis of phosphorodithioate-containing oligonucleotides is also well known in the art, as illustrated by U.S. Pat. No. 5,151,510, the teachings of which are hereby incorporated by reference (See also, e.g., Marshall and Caruthers, *Science*, 259: 1564–1570 (1993) and references cited therein).

In a second preferred embodiment, modified oligonucleotides having tumorigenicity-inhibiting activity according to the invention are in the form of a mixed backbone of chimeric oligonucleotide having one or more region of nucleotides connected by phosphorothioate or phosphorodithioate internucleotide linkages ("phosphorothioate or phosphorodithioate region"), as well as one or more region of nucleotides connected by alkylphosphonothioate or arylphosphonothioate internucleotide linkages ("alkylphosphonothioate region"). In this embodiment, at least one alkylphosphonothioate region preferably includes nucleotides at or near the 5' end and/or the 3' end of the oligonucleotide. Preferably, the alkylphosphonothioate region comprises from about 2 to about 10 contiguous nucleotides connected by alkylphosphonothioate linkages. Preferably, the phosphorothioate or phosphorodithioate region comprises at least 3, and up to about 100 contiguous nucleotides connected by phosphorothioate or phosphorodithioate linkages.

Tumorigenicity-inhibiting modified oligonucleotides according to this embodiment of the invention are synthesized by solid phase methods, alternating chemistries for each region to be synthesized. Phosphorothioate or phosphorodithioate regions are synthesized as described in the first embodiment. Alkylphosphonothioate regions are synthesized by coupling together two or more nucleosides via alkylphosphite linkages, then oxidatively thiolating the alkylphosphite linkages to produce alkylphosphonothioate linkages (see e.g., Agrawal et al., *Nucl. Acids Res.*, 20: 2729–2735 (1993).

In a third preferred embodiment, tumorigenicity-inhibiting modified oligonucleotides according to the invention are in the form of a hybrid oligonucleotide having regions of deoxyribonucleotides ("deoxyribonucleotide regions") and regions of ribonucleotides or 2'-substituted ribonucleotides ("ribonucleotide regions"). Preferably, from about ones to about all of the internucleotide linkages are phosphorothioate or phosphorodithioate linkages. Preferred 2'-substituted ribonucleotides are halo, amino, alkyl, aryl or lower alkyl (1–6 carbon atoms) substituted ribonucleotides, especially 2'-OMe-ribonucleotides. Preferably, at least some of the ribonucleotide regions include nucleotides present at or near the 5' end and/or the 3' end of the oligonucleotide. Most preferably, the ribonucleaotide regions each comprise from about 2 and preferably from about 4 to about 100 contiguous ribonucleotides and/or 2'-substitute oligonucleotides The deoxyribonucleotide regions are optional, and when present may contain from about 1 to about 100 contiguous deoxyribonucleotides. Tumorigenicity-inhibiting modified oligonucleotides according to this embodiment of the invention are typically synthesized by solid phase methods, preferably by the phosphoramidite approach, using deoxynucleotide phosphoramidites for deoxyribonucleotide regions, and ribonucleotide or 2'-substituted ribonucleotide phosphoramidite for ribonucleotide regions.

In a fourth preferred embodiment, tumorigenicity-inhibiting modified oligonucleotides according to that invention are in the form of an oligonucleotide having at its 5' and/or 3' end a cap structure that confers exonuclease resistance to the oligonucleotide. Such modified oligonucleotides preferably also have from 1 to about all modified (non-phosphodiester) internucleotide linkages. Preferred cap structures include lower alkyl ($C_1$–$C_{12}$) or alcohol groups. Preferred modified internucleotide linkages include phosphotriester, phosphoramidate, siloxane, carbonate, carboxymethylester, acetamidate, carbamate,' thioether, bridged phosphoramidate, bridged methylene phosphonate, bridged phosphorothioate, sulfone, phosphorothioate and phosphorodithioate linkages. Tumorigenicity-inhibiting modified oligonucleotides according to this embodiment of the invention are synthesized according to procedures well known in the art (see e.g., Uhlmann and Peyman, *Chemical Reviews*, 90: 43–584 (1990); Schneider and Banner, *Tetrahedron Lett.*, 31: 335 (1990)). For oligonucleotides having cap structures at the 3' end, the cap structure is reversibly attached to the solid-support and is then coupled to the first nucleotide monomer in the synthesis scheme. For oligonucleotides having cap structures at the 5' end, the cap structure is coupled to the end of the oligonucleotide after addition of the last nucleotide monomer in the synthesis scheme.

In a fifth embodiment, tumorigenicity-inhibiting modified oligonucleotides are self-stabilized by having a self-complementary region that hybridizes intramolecularly with the oligonucleotide to form an exonuclease resistant hairpin-like structure (see e.g., Agrawal et al., *Nucleic Acids Res.* 20: 2729–2735 (1993). Modified oligonucleotides according to this embodiment of the invention are generally characterized by having two regions: a DNA MeTase hybridizing region and a self-complementary region. The DNA MeTase hybridizing region has a nucleotide sequence that is complementary to an essential nucleic acid sequence of DNA MeTase. Preferably, this region has from about 6 to about 100 nucleotides. In this embodiment, the oligonucleotide is stabilized, i.e., rendered resistant to exonucleolytic degradation by base-pairing between the target hybridizing region and the self-complementary region and/or by base-pairing between complementary sequences within the self-complementary region. When the oligonucleotide encounters a DNA MeTase nucleic acid molecule having a complementary nucleic acid sequence, base-pairing between the DNA MeTase hybridizing region and the self-complementary region of the oligonucleotide is disrupted and replaced by base-pairing between the DNA MeTase hybridizing region of the oligonucleotide and the complementary nucleic acid sequence of the nucleic acid molecule. This disruption and replacement of base-pairing takes place because the intermolecular base-paired structure formed by the hybrid between the target nucleic acid sequence and the target hybridizing region is more thermodynamically stable than the intramolecular base-paired structure formed by this self-complementary oligonucleotide.

A second form of an oligonucleotide according to this embodiment of the invention operates in a similar way as the first form, but forms a different structures upon self-complementary base-pairing. This alternatives form forms a hammer-like structure. In this form, the self-complementary region contains oligonucleotide sequences that can base pair with other oligonucleotide sequences within the self-complementary region. The self-complementary region may also contain oligonucleotide sequences that are complementary to the tumorigenicity hybridizing region.

The second significant region of self-stabilized oligonucleotides according to the invention is the self-complementary region. The self-complementary region contains oligonucleotide sequences that are complementary to other oligonucleotide sequences within the oligonucleotide. These other oligonucleotide sequences may be within the DNA MeTase hybridizing region or within the self-complementary region, or they may span both regions. The complementary sequences form base pairs, resulting in the formation of a hairpin structure or a hammer-like structure. Either the hairpin structure or the hammer-like structure will presumably have loops of 4 or more nucleotides resulting from non-base-paired nucleotides. The number of base-pairs to be formed by intramolecular hybridization involving the self-complementary region may vary, but should be adequate to maintain a double-stranded structure so that the 3' end is not accessible to endonucleases. Generally, about 4 or more base-pairs will be necessary to maintain such a double-stranded structure. In a preferred embodiment, there are about 10 intramolecular base-pairs formed in the self-stabilized oligonucleotide, with the 10 base pairs being consecutive and involving the 3'-most nucleotides. Of course, the intramolecular base-pairing can be so extensive as to involve every nucleotide of the oligonucleotide. Preferably, this will involve a self-complementary region of about 50 nucleotides or less.

Oligonucleotides according to this embodiment may have from 1 to about all modified internucleotide linkages, as described for the fourth embodiment. Preferably, at least either the DNA MeTase hybridizing region or the self-complementary region, and most preferably both, will contain from about 2 to about all nucleotides being coupled by phosphorothioate and/or phosphorodithioate linkages.

Those skilled in the art will recognize that the features of the various preferred embodiments described above can be combined to produce additional embodiments that may have even greater tumorigenicity-inhibiting activity. Thus, the invention contemplates modified tumorigenicity-inhibiting oligonucleotides having every possible combination of chimeric features, hybrid features, cap structures and self-stabilizing character, all as described herein. Such oligonucleotides are useful as therapeutic agents for inhibition of tumor growth. For such treatment, oligonucleotides may be administered intraperitoneally, intranasally, orally or anally. Preferably, such oligonucleotides will be administered at a concentration of from about 1 to about 50 mg/kg body weight.

The following examples are intended to further illustrate certain preferred embodiments of the invention and are not intended to be limiting in nature.

EXAMPLE 1

Expression of Antisense to the DNA Methyltransferase Gene in Y1 Cells Results in Limited DNA Demethylation Cell Culture and DNA Mediated Gene Transfer To directly inhibit DNA methylation in Y1 cells, either the DNA MeTase antisense expression construct pZαM or a pZEM control vector, Szyf, at al., *J. Biol. Chem.*, 267: 12831–12836 (1992)) was introduced into Y1 adrenocortical carcinoma cells by DNA-mediated gene transfer as follows.

Y1 cells were maintained as monolayers in F-10 medium which was supplemented with 7.25% heat inactivated horse serum and 2.5% heat inactivated fetal calf serum (Immunocorp. Montreal) (Yasumura, et al., *Cancer Res.*, 26: 529–535 (1988)). All other media and reagents for cell culture were obtained from GIBCO-BRL. Y1 cells ($1 \times 10^6$) were plated on a 150 mm dish (Nunc) 15 hours before transfection. The pZαM expression vector (10 µg) was cointroduced into Y1 cells with 1 µg of pUCSVneo as; a selectable marker by DNA mediated gene transfer using the calcium phosphate protocol (Ausubel, et al., 1988, Current Protocols in Molecular Biology, Wiley and Sons, New York). Selection was initiated 48 hours after transfection by adding 0.25 mg/ml G418 (GIBCO-BRL) to the medium. For both constructs, G418 resistant cells were isolated and then cloned in selective medium. For analysis of growth in soft agar, $1 \times 10^3$ cells were seeded in triplicate onto 30 mm dishes (Falcon) with 4 ml of F-10 medium containing 7.5% horse serum, 2.5% FCS, 0.25 mg/ml G418 (for transfectants) and 0.33% agar solution at 37° C. (Freedman and Shin, *Cell*, 3: 355–359 (1974)). Cells were fed with 2 ml of medium plus G418 every two days. Growth was scored as colonies containing $>10^7$ cells, 21 days after plating.

EXAMPLE 2

DNA and RNA Analyses

Preparation of genomic DNA and total cellular RNA, labelling (using the random primer labelling kit from Boehringer Mannheim), blotting RNA on to Hybond-N+ (Amersham), and all other standard molecular biology manipulations were performed according to Ausubel et al., 1988, Current Protocols in Molecular Biology. Wiley and Sons, New York. MspI and HpaII restriction enzymes (Boehringer Mannheim) were added to DNA at a concentration of 2.5 units/ug for 8 h at 37° C. Radionucleotides (3000 mCi/mmol) were purchased from Amersham.

To confirm that the transfectants bear the introduced construct, DNA was prepared from this transfectants and subjected to digestion by either MspI or HpaII, Southern blot analysis and hybridization with a $^{32}P$ labelled 0.6 kb DNA MeTase cDNA fragment. The results demonstrated that the three pZαM transfectants contained significant levels of the DNA MeTase cDNA sequence while the control transfectants were clean.

To test whether the pZαM constructs is expressed in the transfectants and whether the metallothionein promoter is functional in these cells, the transfectants were cultured with 50 μM of ZnSO$_4$, RNA prepared at different time points and subsequently subjected to Northern blot analysis and hybdridization with the $^{32}$P labelled MET 0.6 probe. Transfectants 7 and 9 express substantial amounts of the MET 0.6 cDNA (~1.3 kb chimeric mRNA) even before induction with ZnSO4.

EXAMPLE 3

Demethylation of Specific Genes in Y1 pZαM Transfectants

To verify that expression of pZαM results in demethylation and to determine whether specific genes were demethylated, HpaII/MspI restriction enzyme analysis was employed followed by Southern blotting and hybridization with specific gene probes. HpaII cleaves the sequence CCGG, a subset of the CpG dinucleotide sequences, only when the site is unmethylated while MspI will cleave the same sequence irrespective of its state of methylation. The pattern of HpaII cleavage of specific genes in cells expressing pZαM was compared with that of the parental Y1 or cells harboring only the vector to determine whether the genes are demethylated in the antisense transfectants. The state of methylation of the steroid 21-hydroxylase gene C21 was analyzed first. (Szyf et al., *Proc. Natl. Acad. Sci. USA*, 86: 6853–6857 (1989); Szyf, et al., *Mol. Endocrin.*, 4: 1144–1152 (1990)). This gene is specifically expressed and hypomethylated in the adrenal cortex but is inactivated and hypermethylated in Y1 cells (Szyf et al., *Proc. Natl. Acad. Sci. USA*, 86: 6853–6857 (1989)); Szyf, et al., *Mol. Endocrin.*, 4: 1144–1152 (1990)). DNA prepared from Y1, pZαM (Bernards, et al., *Proc. Natl. Acad. Sci. USA*, 86: 6474–6478 (1989)); Collins et al., *J. Exp. Med.*, 176: 1043–1091 (1992)) and pZαM (Bernards, et al., *Proc. Natl. Acad. Sci. USA*, 86: 6474–6478 (1989)) transfectants was subjected to either MspI or HpaII digestion, Southern blot analysis and hybridization with a 0.36 kb Xba-BamHI fragment containing the enhancer and promoter regions of the C21 gene (see Szyf et al., *Proc. Natl. Acad. Sci. USA*, 86: 6853–6857 (1989); Szyf, et al., *Mol. Endocrin.*, 4: 1144–1152 (1990) for physical map of the probe). This probe detects 0.36 kb and 0.16 kb HpaII fragments when the promoter region is fully demethylated (Szyf et al., *Proc. Natl. Acad. Sci. USA*, 86: 6853–6857 (1989); Szyf, et al., *Mol. Endocrin.*, 4: 1144–1152 (1990)).

The promoter and enhancer region is heavily methylated in Y1 cells and the pZEM transfectants. In contrast, the Y1 pZαM transfectants bear a partially demethylated C21 5' region as indicated by the relative diminution of the 3.8 and 2 kb fragments and the appearance of the fully denothylated faint bands at 0.36 kb as well as the fact that HpaII cleavage yields partial fragments at 0.56 and ~1 kb indicating partial hypomethylation of sites upstream and downstream to the enhancer region.

To determine whether hypouethylation was limited to the enhancer region or spread throughout the C21 gene locus, similar HpaII digestion and Southern blot transfer were performed on different preparations of DNA extracted from Y1 cells, a control pZEM (Bernards, et al., *Proc. Natl. Acad. Sci. USA*, 86: 6474–6478 (1989)) transfectant, and three pZαM antisense transfectants. The filter was hibridized with a 3.8 kb BamHI fragment containing the body of the C21 gene and 3' sequences (Szyf et al., *Proc. Natl. Acad. Sci. USA*, 86: 6853–6857 (1989); Szyf, et al., *Mol. Endocrin.*, 4: 1144–1152 (1990) for physical map). Full demethylation of this region yields a doublet at ~1 kb, a 0.8 kb fragment and a 0.4 kb fragment as well as a number of low molecular weight fragments at 0.1–0.2 kb. The C21 locus is heavily methylated in Y1 cells as well as the control transfectant as indicated by the high molecular weight fragments above 23 kb. Only a faint band is present in the expected 1 kb molecular weight range as well as a partial at 1.9 kb as well as the appearance of new partial fragments in the lower molecular weight range between 1 and 0.4 kb indicating partial hypomethylation at a large number of HpaII sites contained in the 3' region of the C21 gene (Szyf et al., *Proc. Natl. Acad. Sci. USA*, 86: 6853–6857 (1989); Szyf, et al., *Mol. Endocrin.*, 4: 1144–1152 (1990)). The pattern of demethylation, indicated by the large number of partial HpaII fragments, is compatible with a general partial hypomethylation rather than a specific loss of methylation in a distinct region of the C21 gene.

To determine whether demethylation is limited to genes that are potentially expressible in Y1 cells such as the adrenal cortex-specific C21 gene (Szyf, et al., *Mol. Endocrin.*, 4: 1144–1152 (1990)) or if the demethylation is widely spread in the genome, other genes such as the muscle specific MyoD gone as well as the hippocampus specific 5HT1A receptor gene were analyzed; both genes were hypomethylated.

Another class of genes that might have undergone a specific hypomethylation includes the tumor suppressor genes. The state of methylation of two genes from this class was determined, p53 and retinoblastoma (RB) which are both tumor suppressor genes involved in cell cycle regulation. Loss of either one of these gene products has been shown to lead to deregulation of the cell cycle and neoplasia (Bernards, et al., *Proc. Natl. Acad. Sci. USA*, 86: 6474–6478 (1989); Donehoweer, et al., *Nature*, 356: 215–221 (1992)).

Generation of p53 and retinoblastoma (RB) probes by PCR

Oligoprimers for the 5' region of the mouse p53 gene were selected from the published genomic sequence (Accession number: XO1235) (Zakut-Houri, et al., *Nature* 306: 594–597 (1983)) using the Primer selecting program (PC Gene). The 5' primer corresponding to bases 154–172: 5' TCC GAA TCG GTT TCC ACCC 3' (SEQ ID NO 3) and the 3' primer corresponding to bases 472–492 5' GGA GGA TGA GGG CCT GAA TGC 3' (SEQ ID NO 4) were added to a amplification recation mixture containing 100 μg of mouse DNA (from C2C12 cells) using the incubation conditions recommended by the manufacturer (Amersham Hot tub) (1.5 mM MgCl$_2$) and the DNA was amplified for 40 cycles of 2 minutes at 95° C., 2 minutes at 55° C. and 0.5 minutes at 72° C. The reaction products were separated on a low-melt agarose gel (BRL) and the band corresponding to the expected size was excised and extracted according to standard protocols (Ausubel, et al., 1988, Current Protocols in Molecular Biology. Wiley and Sons, New York).

Since the genomic sequence of the mouse RB gene was unavailable through Genbank we reverse transcribed the retinoblastoma mRNA from 0.5 μg of total mouse RNA (from C2C12 cells) using random oligonucleotide primers (Boehringer) with Superscript reverse transcriptase (BRL) under conditions recommended by the manufacturer. The RB sequence was amplified from the reverse transcribed cDNA using oligonucleotides corresponding to bases 2–628 of the published cDNA (Bernards et al., *Proc. Natl. Acad. Sci. USA*, 86: 6474–6478 (1989)). The oligoprimers used were 5' GGA CTG GGG TGA GGA CGG 3' (1–18) (SEQ ID NO 5) and 5' TTT CAG TAG ATA ACG CAC TGC TGG 3' (620–610) (SEQ ID NO 6). The amplification conditions were as described above.

Using a probe to a 300 bp sequence from the 5' region of the mouse RB cDNA, the level of methylation of this gene was determined in Y1 cells transfected with a control vector as well as the pZαM transfectants,. Cleavage of this region with HpaII yields 0.6 kb and 0.1 kb fragments. The RB locus is heavily methylated in the control cells as indicated by hybridization of the probe to high molecular weight fragments. This locus is partially hypomethylated in the pZαM transfectants as indicated by the relative diminution in the intensity of the high molecular weight markers and the partial presence of the 0.6 and 0.15 kb fragments.

EXAMPLE 4

Nearest Neighbor Analysis

Figure 2:
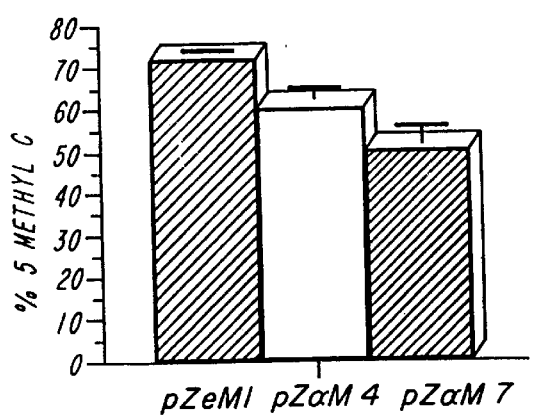
FIG. 2 is a graph showing the state of methylation of total genomic DNA and specific genes in $Y1_p Z\alpha M$ transfectants. The spots on TLC plates corresponding to C and 5-methyl C were scraped and counted in a liquid β scintillation counter. The values represent the means ± SEM.

To determine whether expression of antisense RNA to the DNA MeTase gene leads to a general reduction in the level of methylation of the genome, "nearest neighbor" analysis using [α-$^{32}$P]-dGTP was conducted as described by Razin et al., 1985, in Razin, A., and G. L. Cantoni. (Ed), Biochemistry and Biology of DNA methylation, Allan R. Liss, Inc. N.Y. This assay enables a determination of the percentage of methylated cytosines residing in the dinucleotide sequence CpG. Transfectants and control DNAs were nicked with DNAaseI, nick translated with a single nucleotide [α-$^{32}$P]-dGTP using DNA polymerase I and the labelled DNA was digested to 3' mononucleotide phosphates with micrococal nuclease which cleaves DNA 3' to the introduced α-$^{32}$P. The [α-$^{32}$P] labelled 5α neighbors of dGMP were separated by chromatography on a TLC plate, the resulting spots for dCMP and dC$^{met}$MP were scraped and counted by liquid scintillation. The results of a triplicate experiment presented in FIG. 2a (sample autoradiogram) and b (graphic representation) suggest that a limited but significant reduction in the total level of DNA methylation (12% for transfectant number 4 and 22% for 7) occurred in transfectants expressing the pZαM construct when compared to the control line pZEM.

"Nearest Neighbor" analysis was performed as follows: 2 μg of DNA were incubated at 37° C. for 15 minutes with 0.1 unit of DNAase, 2.5 μl of $^{32}$P-α-dGTP (3000 Ci/mmol from Amersham) and 2 units of Kornberg DNA polymerase (Boehringer) were then added and the reaction was incubated for an additional 25 minutes at 30° C. 50 μl of water were added and the nonincorporated nucleotides were removed by spinning through a microcon column (Anicon) at maximum speed for 30 seconds. The labelled DNA (20 μl) was digested with 70 μg of micrococal nuclease (Pharmacia) in the manufacturer's recommended buffer for 10 hours at 37° C. Equal amounts of radioactivity were loaded on TLC phosphocellulose plates (Merck) and the 3' mononucleotides were separated by chromatography in one dimension (isobutyric acid: H$_2$O: NH$_4$OH in the ratio 66:33:1). The chromatograms were exposed to XAR film (Eastman-Kodak) and the spots corresponding to cytosine and 5-methylcytosine were scraped and counted in a β-scintillation counter.

EXAMPLE 5

In Vitro Tumorigenicity Assays

While control Y1 and Y1 pZEM cells exhibit limited contact inhibition and form multilayer foci, Y1 pZαM transfectants exhibit a more rounded and distinct morphology and grow exclusively in monolayers.

Figure 3:
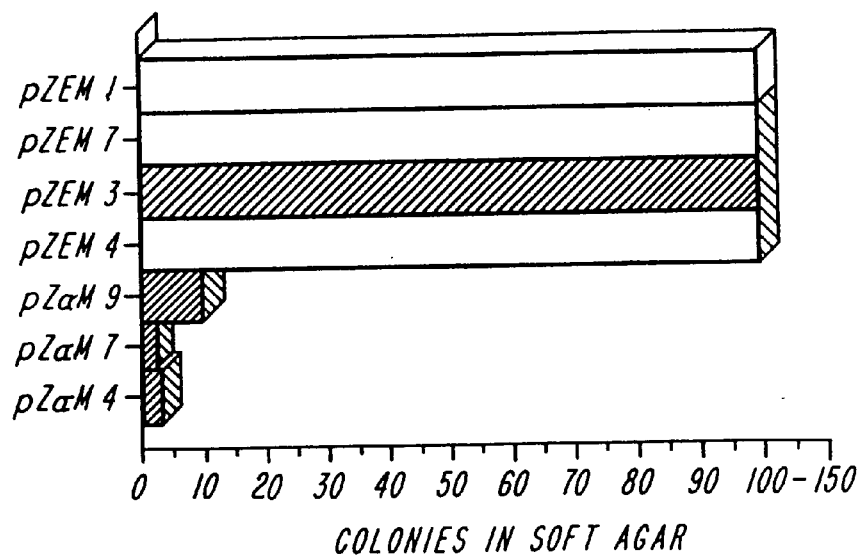
FIG. 3 is a graph indicating anchorage independent growth assay of: Y1 pZEM (clones 4 and 7) and Y1 pZαM transfectants (clones 4, 7 and 9).
Figure 4:
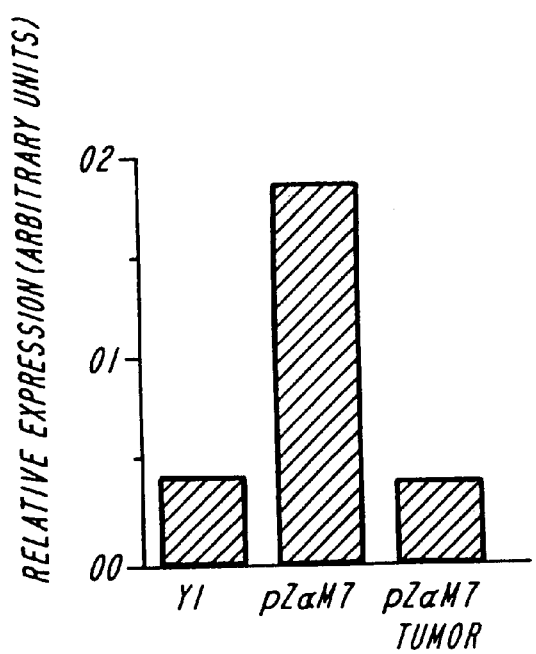
FIG. 4 is a graph indicating a loss of antisense expression in tumors derived from Y1 pZαM transfectants.
Figure 5A:
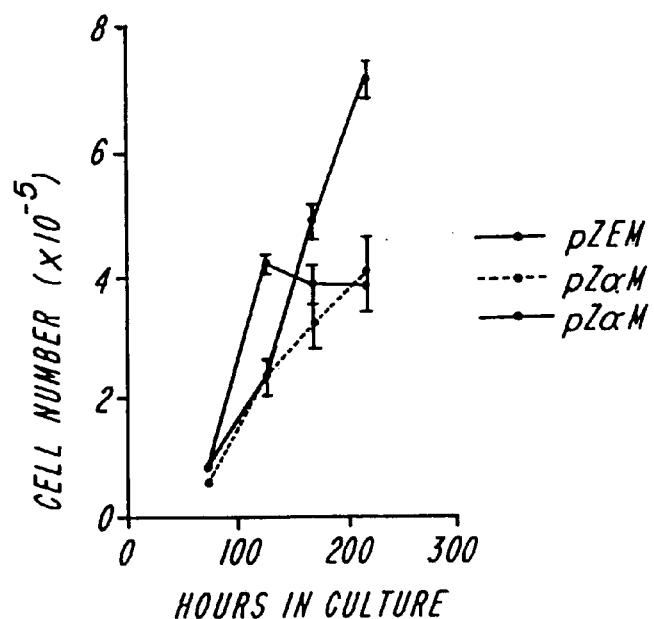
FIG. 5a is a graph showing survival and apoptosis of Y1 pZαM cells as determined by a density restricted growth assay.
Figure 5B:
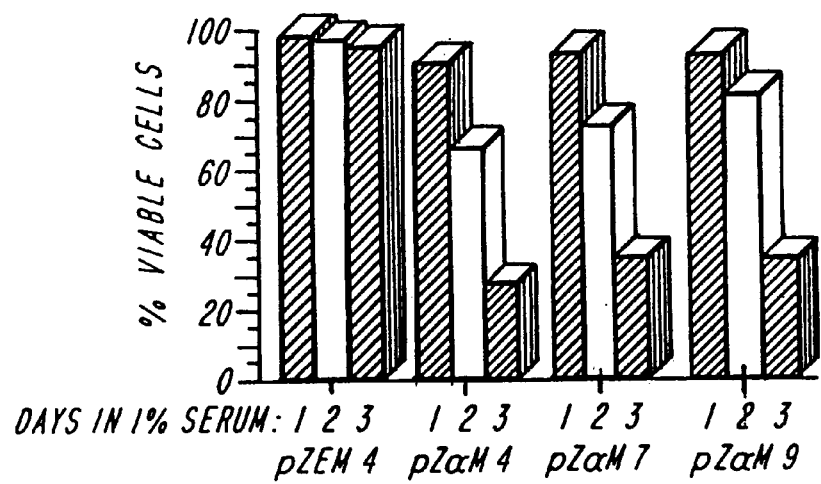
FIG. 5b is a graph showing survival and apoptosis of Y1 pZαM cells in serum deprived medium.

To determine whether the expression of antisense to the DNA MeTase results in reversal of the tumorigenic potential, the ability of the transfectants to grow in an anchorage independent fashion was determined. This assay is considered an indicator of tumorigenicity (Freedman and Shin, Cell 3: 355–359 (1974)). The Y1 pZαM transfectants demonstrate an almost complete loss of ability to form colonies in soft agar, moreover the colonies that do form contain only a few cells as demonstrated (FIG. 3B). Growth on soft agar was quantified by visual examination and presented graphically in FIG. 3. These experiments demonstrate that inhibition of DNA methylation by expression of an antisense message to the DNA MeTase leads to loss of tumorigenicity in vitro.

EXAMPLE 6

In Vivo Tumorigenicity Assays

Syngenic LAF-1 mice (6–8 week old males) were injected subcutaneously (in the flank area) with 10$^6$ cells of each of the Y1 pZαM, Y1 and Y1 pZEM transfectants. Mice were monitored for the presence of tumors by daily palpitation. Mice bearing tumors of greater than 1 cm in diameter were sacrificed by asphyxiation with CO$_2$, tumors wore removed by dissection and homogenized in guanidium isothiocyanate. Mice that were tumor free were kept for ninety days and then sacrificed. RNA was prepared from the tumors by CsCl$_2$ (Ausubel, et al., 1988, Current Protocols in Molecular Biology, Wiley and Sons, New York).

The presence of tumors was determined by palpitation. While all the animals injected with Y1 cells formed tumors two to three weeks post injection, the rate of tumor formation in the animals injected with the pZαM transfectants was significantly lower. The results are shown below in Table I.

TABLE I

| Cell line injected | Tumors | Neovascularization |
| --- | --- | --- |
| Y1 | 6/6 | +++ |
| pZEM 4 | 5/5 | +++ |
| pZαM 4 | 1/6 | --- |
| PZαM 7 | 2/6 | --- |
| pZαM 9 | 2/6 | --- |

EXAMPLE 6A

Figure 6:
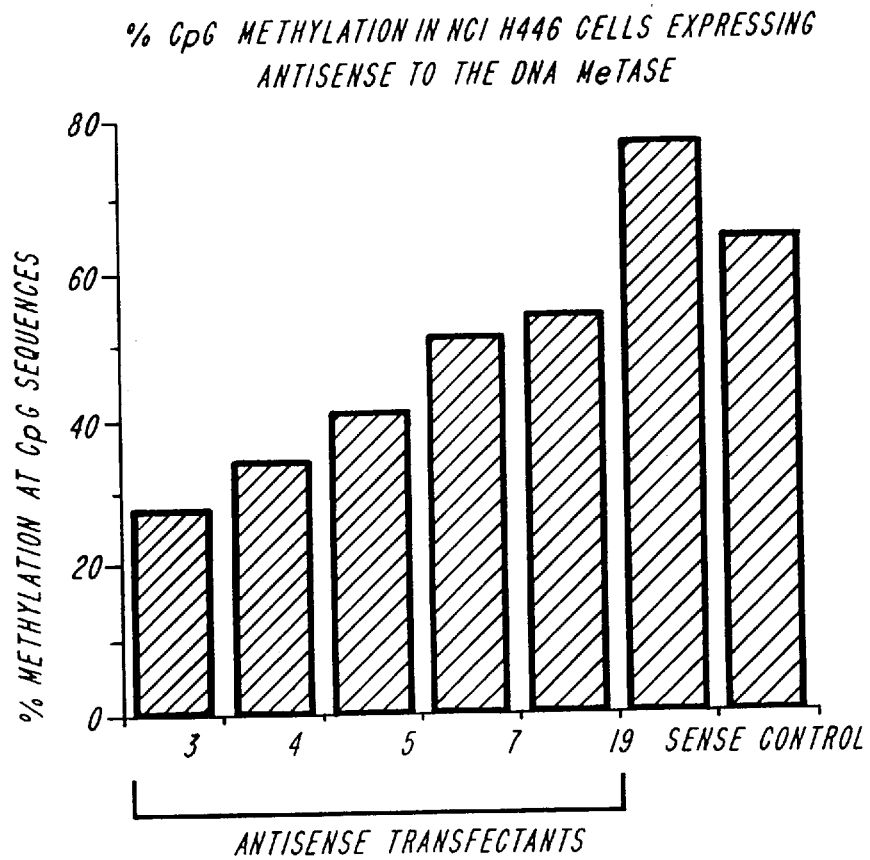
FIG. 6 is a graph showing the percentage of CpG methylation in NCI H446 cells expressing antisense to DNA MeTase and in cells expressing a DNA MeTase sense control oligonucleotide.

In Vivo Inhibition of Tumorigenicity of Human Small Lung Carcinoma Cells in a Nude Mouse System To determine whether inhibition of DNA MeTase by expression of an antisense message results in inhibition of cellular transformation of human carcinomas, a 330 bp sequence containing the translation initiation site (+155–+481) was amplified using the published human DNA MeTase cDNA sequence using the amplification protocol described above in Example 3 (antisense primer was: 5' GCA AAC AGA ATA AAG AAT C 3' (SEQ ID NO 7), the sense primer was: 5' GTA TGG TGG TTT GCC TGG T 3' (SEQ ID NO 8)). The 330 bp sequence was subcloned in the antisense orientation into the expression vector pZEM as described above for the mouse antisense. A human small lung carcinoma cell line NCI H446 was cotransfected with either an antisense DNA MeTase expression vector or a control sense expression vector and a plasmid conferring resistance to hygromycin using transfection protocols as described above. Hygromycin resistant colonies were selected and the presence of the transfected antisense was verified by digestion with EcoRI, Southern blot transfer and hybridization with a 0.4 kb human DNA MeTase cDNA probe. Demethylation of genomic DNA of cells expressing the antisense was verified by nearest neighbor analysis (FIG. 6) as described above and by hybridization with specific gone probes. The gene encoding the IGF-1 growth factor was demethylated in antisense transfectants but not sense controls.

To determine whether the expression of antisense to DNA MeTase results in reversal of the tumorigenic potential, the ability of the transfectants to grow in an anchorage independent fashion was analyzed. The: antisense transfectants lost their ability to form colonies in soft agar indicating loss of tumorigenicity in vitro.

Tumor growth in nude mice was evaluated as follows::

4 groups of mice were injected with $10^6$ NCI H446 cells transfected with the pZαM 5' human MeTase (0.4 kb) antisense expression plasmid and the hygromycin resistance plasmid.

1 group of mice was injected with $10^6$ NCI H446 cells transfected with the pZαM 5' human MeTase (0.4 kb) sense expression plasmid and the hygromycin resistance plasmid.

1 group of mice was injected with $10^6$ NCI H446 cells bearing the hygromycin resistance plasmid.

1 group of mice was injected with $10^6$ NCI H446 lung cell line.

The mice were followed for in excess of 12 weeks. The results are shown in Table II. These results demonstrate that expression of antisense to the DNA MeTase inhibited turigenesis In vivo.

TABLE II

TUMOR DEVELOPMENT IN NUDE MICE

| Transfectant clones | Number of mice injected | Number of mice developing tumors | Latency period of mice developing tumors |
| --- | --- | --- | --- |
| pZαM[1] #3 | 3 | 0 | >12 weeks |
| pZαM #3 | 3 | 0 | >12 weeks |
| pZαM #3 | 2 | 0 | >12 weeks |
| pZαM #3 | 3 | 0 | >12 weeks |
| pZM[2] #5 | 3 | 2 | 5 weeks |
| Hyg only[3] | 3 | 3 | 5 weeks |
| Tumor only[4] | 3 | 3 | 3 weeks |

[1]NCI H446 cells transfected with the pZαM 5' human MeTase (0.4 kb) antisense expression plasmid and the hygromycin resistance plasmid
[2]NCI H446 cells transfected with the pZαM 5' human MeTase (0.4 kb) sense expression plasmid and the hygromycin resistance plasmid
[3]NCI H446 cells bearing the hygromycin resistance plasmid
[4]NCI H446 lung cell line Neovascularization Many lines of evidence suggest that angiogenic potential and metastatic potential of cell lines area directly related (Liotta, at al., *Cell,* 64: 327–336 (1991)). The tumors that do arise from the pZαM transfectants exhibit very limited neovascularization while tumors that formed in the animals that were injected with Y1 cells or control transfectants were highly vascularized.

RNA from a tumor arising from the Y1pZαM transfectant was isolated and the level of expression of the 0.6 kb antisense message was compared with that observed for the transfectant line in vitro. The isolated RNAs were subjected to Northern blot analysis and hybridization with a $^{32}P$ labelled MET 0.6 fragment. The filter was stripped of its radioactivity and was rehybridized with a $^{32}P$ labelled oligonucleotide probe for 18S rRNA as previously described (Szyf et al., *Mo. Endocrinol.,* 4: 1144–1152 (1990)). The autoradiograms were scanned and the level of expression of MET 0.6 was determined relative to the signal obtained with the 18S probe. The expression of the antisense message is significantly reduced in the tumors. Thus, it appears that expression of an antisense message to the DNA MeTase is incompatible with tumorigenesis. Apparently, the small number of tumors that did form in animals injected, with the pZαM transfectants were derived from revertants that lost expression of the antisense to the DNA MeTase under the selective pressure in vivo.

EXAMPLE 7

Relationship of Serum Deprivation and Expression of pZαM in Y1 Cells to Apoptotic Death Program Tumor cells exhibit limited dependence on serum and are usually capable of serum independent growth (Barns and Sato, *Cell,* 22: 649–655 (1980)). Factors present in the serum are essential for the survival of many nontumorigenic cells. Several lines of evidence have recently suggested that the enhanced survivability of tumorigenic cells is associated with inhibition of programmed cell death. For example, the oncogene bcl-2 is not a stimulator of cell proliferation but rather causes inhibition of apoptosis (Strasser, et al., *Nature,* 348: 331–333 (1990)). The tumor suppressor p53 can induce apoptosis in a human colon tumor derived line (Shaw, et al., *Proc. Natl. Acad. Sci.,* 89: 4495–4499 (1992)) and certain chemotherapeutic agents have been shown to incude apoptosis in cancer cells (Collins et al, *J. Exp. Med.,* 176: 1043–1091 (1992)).

Observation of the pZαM transfectants indicated that they exhibited enhanced dependence on serum and limited survivability under serum deprived conditions. The effects of serum starvation were studied on pZαM transfectants. pZαM transfectants and control Y1 pZEM transfectants ($3\times10^5$ per well) were plated in low serum medium (1% horse serum) in six well plates, harvested every 24 hours and tested for viability by trypan blue staining (FIG. 6B). While the control cells exhibited almost 100% viability up to 72 hours after transfer into serum deprived medium, the Y1pZαM cells showed up to 75% loss of viability at 48 hours (FIG. 6B).

Y1 pZαM cells were plated in starvation medium (1% horse serum) and harvested at 24 hour intervals. Total cellular DNA was isolated from the cells and was subjected to electrophoresis on a 1.5% agarose gel followed by transfer to nylon membrane and hybridization with random labeled Y1 genomic DNA. After 48 hours in serum starved conditions, pZαM transfectants exhibit the characteristic 180 bp internucleosomal DNA ladder while the control pZEM transfectants show no apoptosis at this time point.

Y1 pZαM cells were serum starved for 24 hours (2% horse serum), harvested and analyzed by electron microscopy as follows. Cells were fixed in glutaraldehyde (2.5%) in cacodylate buffer (0.1M) for one hour and further fixed in 1% osmium tetroxide. The samples were dehydrated in ascending alcohol concentrations and propylene oxide followed by embedding in Epon. Semi-thin sections (1 μM) were cut from blocks with an ultramicrotome, counterstained with uranil acetate and lead citrate. Samples were analyzed using a Philips 410 electron microscope (Maysinger, et al., *Neurochem. Intl.,* 23: 123–129 (1993)).

Electron microscopy of control Y1 pZEM and Y1 pZαM transfectants at various magnifications revealed that control cells have a fine uniform nuclear membrane whereas the pZαM cells exhibit the cardinal markers of apoptosis (Wyllie, et al., *Histochem. J.,* 13: 681–692 (1981)) condensation of chromatin and its margination at the nuclear periphery, chromatin condensation, nuclear fragmentation, formation of apoptotic bodies and cellular fragmentation. This set of experiments suggests that one possible mechanism through whch demethylation can inhibit tumorigenesis is by eliminating the inhibition of programmed cell death.

EXAMPLE 8

In this experiment, human small lung carcinoma cells (NCI H446) were treated with 5 μl lipofectin reagent (Gibco BRL) and oligo (5 μl) in 1 ml serum free media for approximately 4 hours (final oligo concentrations=5 μM). The media was then replaced with 2 ml normal medium and oligo was added to obtain a concentration of 5 μM. Medium and oligo were then replaced daily for the following 3 days. The oligos used were the following:

34: DW2-34B (antisense phosphodiester) 5' CAT CTG CCA TTC CCA CTC TA 3' (SEQ ID NO 9)

35: DW2-35C 5' Phosphorothioate of 34 (SEQ ID NO 10)

36: DW2-36C (random control phosphodiester) 5' CTG ACT GCC AAC TAT GAA CA 3' (SEQ ID NO 11)

37: DW2-37D 5' Phosphorothioate of 36 (SEQ ID NO 12)

The cells grew reasonably well, however throughout the growth period, there were less cells in the wells treated with oligo 35 than in the others and many cells in these wells were floating. Several cells were also deteched in the wells treated with oligo 37.

Experiment A

In this experiment, cells were grown in presence of the oligos for longer than in the previous experiment (14 days). The initial treatment comprised of 5 μl lipofectin and 10 μl oligo in 1 ml media. Subsequently, media was changed and oligo added (10 μl in 2 ml) daily for 9 days and for the final 4 days, to avoid losing cells that were floating but not necessarily dead, the medium was changed only once and oligo added to the medium every other day.

Cells for this experiment were slow to start growing. During the first week of treatment with oligo, cells remained quite sparse and a very high proportion of cells were observed to be round and/or floating. During the second week, as the cells started to grow more nicely, clumps of cells appeared in the control wells and in the 34 and 36. In the wells treated with oligo 35, there were consistently fewer cells and a higher proportion of floating cells than in control wells. In addition, the 35 cells that remained attached were more elongated than controls. Similar features were observed to a lesser extent in the 37 cells. Toward the end of the experiment, the control cells seemed more elongated than they had been previously, though significantly less than the 35 cells. Wells 34 and 36 contained more large clusters of cells than the others (even controls). On the whole, there were fewer clumps in wells 35 and 37 than in all the others. Oligo 34 (antisense phosphodiester) appeared to have no effect on cell morphology.

Figure 7:
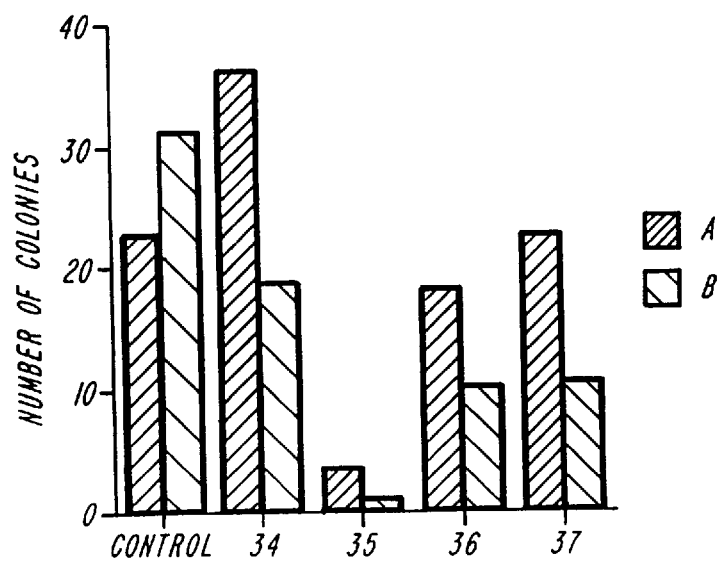
FIG. 7 shown the ability of NCI H446 cells treated with antisense and control oligonucleotides to grow in an anchorage independent fashion in soft agar.

To determine whether treatment with DNA MeTase antisense oligonucleotides inhibits tumorigenesis in vitro, the ability of the treated cells to grow in an anchorage independent fashion was determined. Two sets of cells were analyzed: Set A was treated for 15 days and Set B was treated for 9 days. The number of cells were determined by inspection with the naked eye 18 days after plating. As shown in FIG. 7, the cells treated with oligo 35 have lost the ability to grow in an anchorage independent fashion in vitro, indicating inhibition of tumorigenicity In vitro.

Experiment B

Given the fact that cells did not grow very well in the initial stages of experiment A, more cells (~150,000 instead of 80,000) were plated to repeat the experiment. These cells were treated with lipofectin (5 μl) and oligo (10 μl) on day 1 and then the medium was changed and 10 μl oligo were added daily for three days and for the next four days, 10 μl oligo were added daily and the medium was changed only once.

After the 8 days of treatment, cells in wells 36 and 37 were similar in appearance to the control wells. Only the cells treated with oligo 35 looked significantly different from the others in that there had been less growth and cells appeared on the whole less "clumpy" than controls. The cells treated with oligo 35 again lost their ability to form colonies in soft agar, indicating reversal of tumorigenicity In vitro.

Dose Curve:

Cells were treated for 5 days with different doses of oligo 35 (antisense phosphorothioate): 0.5 μM, 1.5 μM, 5 μM, 15 μH and 50 μN.

| Well | Initial lipofectin* | Initial oligo | Daily oligo |
|---|---|---|---|
| control | 5μl | 0 | 0 |
| 0.5μM | 5μl | 1μl(1μM) | 1μl(0.5μM) |
| 1.5μM | 5μl | 3μl(3μM) | 3μl(1.5μM) |
| 5μM | 5μl | 10μl(10μM) | 10μl(5μM) |
| 15μM | 5μl | 30μl(30μM) | 30μl(15μM) |
| 50μM | 5μl | 100μl(100μM) | 100μl(50μM) |

*Lipofectin reagent (Gibco BRL)

Initial treatment with lipofectin and oligo were in 1 ml medium and subsequently, cells were in 2 ml medium.

Treatment with oligo 35 resulted in dramatic changes in cell morphology. At all doses, formation of larger clusters of cells was inhibited with respect to the controls. As oligo concentration increased, cells became less clumpy and more elongated. Increasing numbers of floating cells appeared, many of which were alive as revealed by viability counts.

Upon treatment with 15 μM oligo, cells became dramatically elongated and no clumps of cells could be seen (see pictures). A high proportion of cells were floating, however viability was found to be over 50%, suggesting that many of the floating cells are still alive.

EXAMPLE 9

In Vivo Inhibition of Tumorigenicity Using Anitsense Technology

In vivo inhibition of DNA methyl transferase expression and tumorigenesis can be achieved by administration of the antisense oligonucleotides of the present invention to mammals. For example, administration into a mouse can be by slow infusion pump at a rate of about 0.5–3.0 nMoles/hr (about 0.15–1.0 mg of an oligonucleotide 20-mer per kg of body weight). Alternatively, intravenous injection of about 1–5 mg of the oligonucleotide per kg body weight can be made into the tail vein. After about 10 to 21 days the tumors can be excised and analyzed for DNA methyl transferase expression as well as by observing the weight and morphology of the tumors. Tumors and DNA methyl transferase levels of mice treated with a control oligonucleotide can be compared.

From the foregoing it will be appreciated that, although specific embodiments of the invention have been described herein for purposes of illustration, various modifications may be made without deviating from the spirit and scope of the invention.

What is claimed is:

1. A method for inhibiting tumor growth comprising providing to a cell that expresses a DNA methyltransferase gene an effective tumor growth-inhibiting amount of an antisense oligonucleotide complementary to DNA methyltransferase mRNA.

2. The method according to claim 1, wherein the oligonucleotide anneals to a coding sequence of the DNA methyltransferase mRNA.

3. The method according to claim 1, wherein the oligonucleotide binds to the start or stop sequence of DNA methyltranferase mRNA.

4. The method according to claim 3, wherein the oligonucleotide is self-stabilized.

5. The method according to claim 1, wherein the oligonucleotide is stabilized by methylphosphonothioate internucleotide linkages, phosphorothioate internucleotide linkages, methylphosphonate internucleotide linkages, phosphoramidate internucleotide linkages, a 3' end cap, or a 3' hair-pin loop structure.

6. The method according to claim 1, wherein the oligonucleotide is a mixed phosphate backbone oligonucleotide having an internal sequence that activates RNase H and that is flanked on one or both sides by sequences that are unable to activate RNase H.

7. The method according to claim 1, wherein the oligonucleotide has the sequence 5'-CATCTGCCATTCCCACTCTA-3' (SEQ ID NO 1).

8. The method according to claim 1, wherein the oligonucleotide has the sequence 5'-TTGGCATCTGCCATTCCCACTCTA-3' (SEQ ID NO 2).

* * * * *